United States Patent
Wang et al.

(10) Patent No.: US 12,240,938 B2
(45) Date of Patent: Mar. 4, 2025

(54) 2,2-DIMETHYL-1,3-DIOXOLAN-4-YL-METHYL 2-BROMO-2,2-DIFLUOROACETATE, WATERBORNE POLYURETHANE, AND PREPARATION METHODS THEREOF

(71) Applicants: Hangzhou Transfar Fine Chemical Co., Ltd., Hangzhou (CN); Hangzhou Normal University, Hangzhou (CN)

(72) Inventors: Shengpeng Wang, Hangzhou (CN); Bajin Chen, Hangzhou (CN); Weiming Xu, Hangzhou (CN); Jinxing Song, Hangzhou (CN); Pengfei Zhang, Hangzhou (CN); Xiaojun Wang, Hangzhou (CN); Bencheng Yu, Hangzhou (CN); Youju Huang, Hangzhou (CN); Xiaobo Yang, Hangzhou (CN)

(73) Assignees: Hangzhou Transfar Fine Chemical Co., Ltd., Hangzhou (CN); Hangzhou Normal University, Hangzhou (CN)

( * ) Notice: Subject to any disclaimer, the term of this patent is extended or adjusted under 35 U.S.C. 154(b) by 598 days.

(21) Appl. No.: 17/565,755

(22) Filed: Dec. 30, 2021

(65) Prior Publication Data

US 2023/0103217 A1    Mar. 30, 2023

(30) Foreign Application Priority Data

Aug. 31, 2021    (CN) .......................... 202111009687.1

(51) Int. Cl.
*C08G 18/38*    (2006.01)
*C07D 317/22*    (2006.01)
(Continued)

(52) U.S. Cl.
CPC ....... *C08G 18/3812* (2013.01); *C07D 317/22* (2013.01); *C08G 18/0823* (2013.01); *C08G 18/10* (2013.01); *C08G 18/222* (2013.01); *C08G 18/3206* (2013.01); *C08G 18/3802* (2013.01); *C08G 18/381* (2013.01); *C08G 18/6692* (2013.01); *C08G 18/7621* (2013.01);
(Continued)

(58) Field of Classification Search
None
See application file for complete search history.

(56) References Cited

U.S. PATENT DOCUMENTS

| 5,744,569 A * | 4/1998 | Bruchmann ....... C08G 18/2835 549/39 |
| 2020/0299451 A1* | 9/2020 | Chen .................. C08G 18/3812 |

* cited by examiner

*Primary Examiner* — Rachel Kahn
(74) *Attorney, Agent, or Firm* — Hunton Andrews Kurth LLP

(57) ABSTRACT

Disclosed are (2,2-dimethyl-1,3-dioxolan-4-yl)methyl 2-bromo-2,2-difluoroacetate, a waterborne polyurethane, and preparation methods thereof. The (2,2-dimethyl-1,3-dioxolan-4-yl)methyl 2-bromo-2,2-difluoroacetate could be used as a modified monomer for preparing a waterborne polyurethane, and substituents at a C2 position of the (2,2-dimethyl-1,3-dioxolan-4-yl)methyl 2-bromo-2,2-difluoroacetate are two fluorine atoms and one bromine atom. When it is used for preparing the waterborne polyurethane, fluorine and bromine groups are introduced into the structure of the waterborne polyurethane, and the resultant waterborne polyurethane exhibits good moisture resistance and flame retardance.

2 Claims, 2 Drawing Sheets

(51) Int. Cl.
*C08G 18/08* (2006.01)
*C08G 18/10* (2006.01)
*C08G 18/22* (2006.01)
*C08G 18/32* (2006.01)
*C08G 18/66* (2006.01)
*C08G 18/76* (2006.01)
*B01J 23/04* (2006.01)
*B01J 31/02* (2006.01)
*B01J 31/04* (2006.01)
*B01J 31/12* (2006.01)
*C07D 317/24* (2006.01)

(52) U.S. Cl.
CPC ............ *B01J 23/04* (2013.01); *B01J 31/0201* (2013.01); *B01J 31/04* (2013.01); *B01J 31/121* (2013.01); *B01J 2531/12* (2013.01); *B01J 2531/13* (2013.01); *C07D 317/24* (2013.01)

2,2-DIMETHYL-1,3-DIOXOLAN-4-YL-METHYL 2-BROMO-2,2-DIFLUOROACETATE, WATERBORNE POLYURETHANE, AND PREPARATION METHODS THEREOF

CROSS REFERENCE TO RELATED APPLICATION

This patent application claims the benefit and priority of Chinese Patent Application No. 202111009687.1 filed on Aug. 31, 2021, the disclosure of which is incorporated by reference herein in its entirety as part of the present application.

TECHNICAL FIELD

The present disclosure relates to the technical field of printing and dyeing auxiliaries, and in particular to (2,2-dimethyl-1,3-dioxolan-4-yl)methyl 2-bromo-2,2-difluoroacetate, a waterborne polyurethane, and preparation methods thereof.

BACKGROUND ART

A printing and dyeing auxiliary can endow a fabric with different functions, and plays an irreplaceable role in the textile field. A waterborne polyurethane (PU) which is used with water as a medium, is safe and nonflammable, and pollution-free. It retains the excellent performance of a traditional solvent-based polyurethane, such as endowing a fabric with excellent softness, fullness, good elasticity, smoothness, good hand feeling and antistatic property, and thus is an ideal printing and dyeing auxiliary. However, the existing waterborne polyurethane generally has the defects of easy water absorption and moisture regain, poor flame retardance and the like.

For example, CN101545207A discloses an anti-pilling finishing agent for pure cotton knitted fabrics and a preparation method thereof. The method includes the following steps: adding melamine and isophorone into a container, heating and stirring the resulting mixture, dropwise adding a mixed solution which is formed by dissolving isophorone diisocyanate in isopropanol, then adding a catalyst, heating and mixing uniformly the resulting mixture, cooling, then adding isopropanol, a capping agent, an accelerator and water thereto, and subjecting the resulting mixture to a reaction, then heating to an ambient temperature, and continuously stirring to obtain a waterborne polyurethane. The waterborne polyurethane could be directly used as an anti-pilling agent and has advantages of not easily yellowing textiles and being environment-friendly. However, the prepared waterborne polyurethane still has the problems of easy water absorption and moisture regain, and poor flame retardance.

SUMMARY

An object of the present disclosure is to provide (2,2-dimethyl-1,3-dioxolan-4-yl)methyl 2-bromo-2,2-difluoroacetate, a waterborne polyurethane and preparation methods thereof. The (2,2-dimethyl-1,3-dioxolan-4-yl)methyl 2-bromo-2,2-difluoroacetate of the present disclosure is used as a modified monomer for preparing the waterborne polyurethane, and the resultant waterborne polyurethane has good moisture resistance and flame retardance.

In order to realize the aforementioned object of the present disclosure, the present disclosure provides the following technical solutions.

The present disclosure provides (2,2-dimethyl-1,3-dioxolan-4-yl)methyl 2-bromo-2,2-difluoroacetate, having a structure of Formula I:

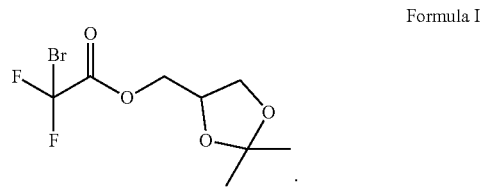

Formula I

The present disclosure provides a method for preparing the (2,2-dimethyl-1,3-dioxolan-4-yl)methyl 2-bromo-2,2-difluoroacetate as described in the aforementioned solutions, including the following steps:
  mixing a 2-bromo-2,2-difluoroacetate, Solketal and an alkaline catalyst, and
  subjecting the resulting mixture to an ester exchange reaction to obtain the (2,2-dimethyl-1,3-dioxolan-4-yl)methyl 2-bromo-2,2-difluoroacetate having a structure of Formula I,
  wherein a molar ratio of the 2-bromo-2,2-difluoroacetate to Solketal is in the range of 1:1-5.

In some embodiments, the alkaline catalyst includes one or more of a hydroxide, a carbonate, a bicarbonate, sodium hydride, and sodium alkoxide.

In some embodiments, the 2-bromo-2,2-difluoroacetate is methyl 2-bromo-2,2-difluoroacetate or ethyl 2-bromo-2,2-difluoroacetate.

In some embodiments, a mass ratio of the 2-bromo-2,2-difluoroacetate to the alkaline catalyst is in the range of 1:0.01-0.2.

In some embodiments, the ester exchange reaction is performed at a temperature of 80-140° C.

In some embodiments, the ester exchange reaction is performed for 5-25 h.

The present disclosure provides use of the (2,2-dimethyl-1,3-dioxolan-4-yl)methyl 2-bromo-2,2-difluoroacetate as described in the aforementioned solutions or the (2,2-dimethyl-1,3-dioxolan-4-yl)methyl 2-bromo-2,2-difluoroacetate prepared by the method as described in the aforementioned solutions in the preparation of a waterborne polyurethane.

The present disclosure provides a waterborne polyurethane, which is prepared from raw materials comprising, in parts by mass,
  15-40 parts of a polyisocyanate monomer, 45-65 parts of a polymer polyol, 5-25 parts of a fluorine-containing modified monomer, a solid Lewis acid catalyst, 0.5-8 parts of a small-molecule chain extender, 3-10 parts of an ionic hydrophilic chain extender, more than 0 and not more than 12 parts of an ionic neutralizer, and water,
  wherein a mass ratio of the fluorine-containing modified monomer to the solid Lewis acid catalyst is in the range of 1:0.005-0.05; and
  the fluorine-containing modified monomer is the (2,2-dimethyl-1,3-dioxolan-4-yl)methyl 2-bromo-2,2-difluoroacetate as described in the aforementioned solutions.

The present disclosure provides a method for preparing the waterborne polyurethane as described in the aforementioned solutions, including the following steps:
(1) mixing a part of the polyisocyanate, the fluorine-containing modified monomer and the solid Lewis acid catalyst, and subjecting the resulting mixture to a first nucleophilic addition reaction to obtain a NCO-terminated fluorinated prepolymer;
(2) mixing the polymer polyol with the rest of the polyisocyanate monomer, subjecting the resulting mixture to a second nucleophilic addition reaction to obtain a second nucleophilic addition reaction product; adding the NCO-terminated fluorinated prepolymer, the small-molecule chain extender and the ionic hydrophilic chain extender into the second nucleophilic addition reaction product, and subjecting the resulting mixture to a chain extension reaction, to obtain a chain extension reaction product, adding a first catalyst into the chain extension reaction product, and subjecting the resulting mixture to a third nucleophilic addition reaction to obtain a fluorinated and modified polyurethane prepolymer; and
(3) adding an ionic neutralizer into the fluorinated and modified polyurethane prepolymer, and subjecting the resulting mixture to a neutralization reaction, and then adding water thereto for emulsification and dispersion to obtain the waterborne polyurethane.

The present disclosure provides (2,2-dimethyl-1,3-dioxolan-4-yl)methyl 2-bromo-2,2-difluoroacetate, having a structure of Formula I:

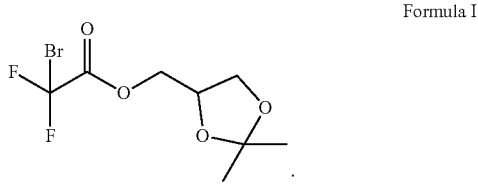

Formula I

The (2,2-dimethyl-1,3-dioxolan-4-yl)methyl 2-bromo-2,2-difluoroacetate according to the present disclosure, in which substituents at a C2 position are two fluorine atoms and one bromine atom, when used as the modified monomer, exhibits certain hydrophobicity, and meanwhile further improves moisture-proof and flame-retardant performance of the modified monomer. When it is used in the preparation of the waterborne polyurethane, fluorine and bromine groups are introduced into the structure of the waterborne polyurethane, and the resultant waterborne polyurethane has good moisture-proof and flame-retardant performance due to the containing of fluorine and bromine atoms.

DETAILED DESCRIPTION OF THE EMBODIMENTS

Figure 1:
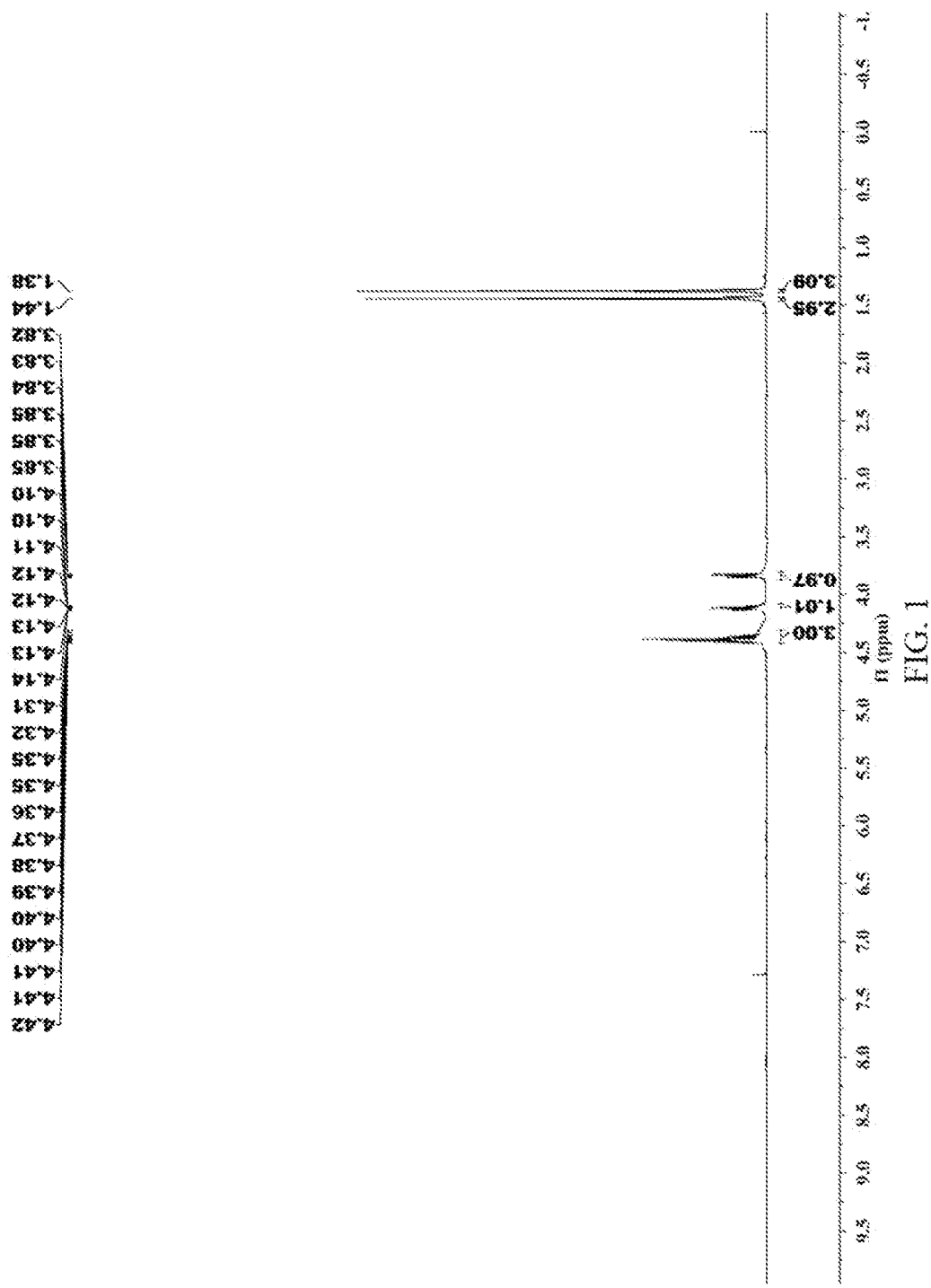
FIG. 1 shows the hydrogen-nuclear magnetic resonance ($^1$H NMR) spectrum of the (2,2-dimethyl-1,3-dioxolan-4-yl)methyl 2-bromo-2,2-difluoroacetate as prepared in Example 1.

The present disclosure provides (2,2-dimethyl-1,3-dioxolan-4-yl)methyl 2-bromo-2,2-difluoroacetate, having a structure of Formula I:

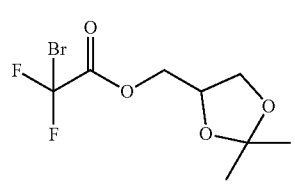

Formula I

The present disclosure provides a method for preparing the (2,2-dimethyl-1,3-dioxolan-4-yl)methyl 2-bromo-2,2-difluoroacetate as described in the aforementioned solutions, including the following steps: mixing a 2-bromo-2,2-difluoroacetate, Solketal and an alkaline catalyst, and subjecting the resulting mixture to an ester exchange reaction, to obtain the (2,2-dimethyl-1,3-dioxolan-4-yl)methyl 2-bromo-2,2-difluoroacetate having the structure of Formula I,
wherein a molar ratio of the 2-bromo-2,2-difluoroacetate to Solketal is in the range of 1:1-5.

In the present disclosure, all the raw materials used are well-known commercial products in the art, unless otherwise specified.

In some embodiments of the present disclosure, the 2-bromo-2,2-difluoroacetate is methyl 2-bromo-2,2-difluoroacetate or ethyl 2-bromo-2,2-difluoroacetate. In some embodiments, the alkaline catalyst includes one or more of a hydroxide, a carbonate, a bicarbonate, sodium hydride, and sodium alkoxide, and preferably includes one or more of an alkali metal hydroxide, an alkali metal carbonate, an alkali metal bicarbonate, sodium hydride, sodium methoxide, and sodium ethoxide. In some embodiments of the present disclosure, the alkali metal hydroxide is sodium hydroxide and/or potassium hydroxide. In some embodiments, the alkali metal carbonate is sodium carbonate and/or potassium carbonate. In some embodiments, the alkali metal bicarbonate is sodium bicarbonate and/or potassium bicarbonate. In some embodiments, when the alkaline catalyst includes more of the aforementioned substances, the mass of each alkaline catalyst is equivalent.

In the present disclosure, a molar ratio of the 2-bromo-2,2-difluoroacetate to Solketal is in the range of 1:1-5, preferably 1:2-4, and more preferably 1:2.5-3.5. In the present disclosure, when the molar dosage of Solketal is greater than that of the 2-bromo-2,2-difluoroacetate, Solketal can also act as a solvent, which is beneficial to the full completion of the ester exchange reaction.

In some embodiments of the present disclosure, a mass ratio of the 2-bromo-2,2-difluoroacetate to the alkaline catalyst is in the range of 1:0.01-0.2, preferably 1:0.05-0.15, and more preferably 1:0.08-0.12.

In the present disclosure, there is no special requirement on the mixing process of the 2-bromo-2,2-difluoroacetate, Solketal and the alkaline catalyst, and a mixing process well known in the art may be adopted, as long as all the raw materials could be uniformly mixed.

In some embodiments of the present disclosure, the ester exchange reaction is performed at a temperature of 80-140° C., preferably 90-130° C., and more preferably 100-120° C. In some embodiments, the ester exchange reaction is performed for 5-25 h, preferably 10-20 h, and more preferably 13-16 h. In some embodiments of the present disclosure, the ester exchange reaction is carried out under a stirring condition. In the present disclosure, there is no special requirement on the stirring speed, and a stirring speed well known in the art may be adopted.

In embodiments of the present disclosure, the ester exchange reaction is carried out according to Equation (1):

Equation (1)

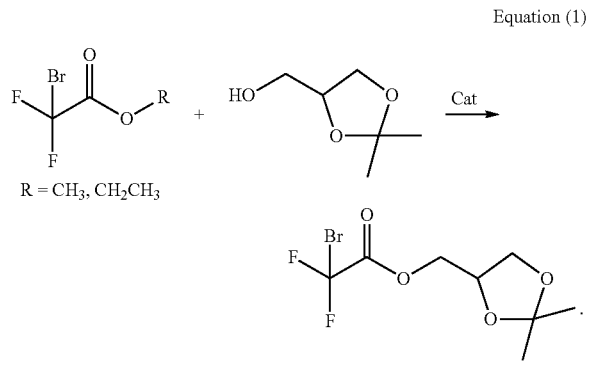

In some embodiments of the present disclosure, after the ester exchange reaction is completed, the obtained product of the ester exchange reaction is distilled under reduced pressure, and a fraction under the conditions of 104-106° C./25 mmHg is collected to obtain the (2,2-dimethyl-1,3-dioxolan-4-yl)methyl 2-bromo-2,2-difluoroacetate having the structure of Formula I.

The method according to the present disclosure has simple operations, an environment-friendly process and a high product yield.

The present disclosure provides use of the (2,2-dimethyl-1,3-dioxolan-4-yl)methyl 2-bromo-2,2-difluoroacetate as described in the aforementioned solutions or the (2,2-dimethyl-1,3-dioxolan-4-yl)methyl 2-bromo-2,2-difluoroacetate prepared by the method as described in the aforementioned solutions in the preparation of a waterborne polyurethane. The (2,2-dimethyl-1,3-dioxolan-4-yl)methyl 2-bromo-2,2-difluoroacetate is preferably used as a modified monomer for preparing the waterborne polyurethane. Substituents at a C2 position of the (2,2-dimethyl-1,3-dioxolan-4-yl)methyl 2-bromo-2,2-difluoroacetate are two fluorine atoms and one bromine atom, so that the modified auxiliary monomer exhibits further improved moisture-proof and flame-retardant performance and meanwhile certain hydrophobicity. When it is used in the preparation of the waterborne polyurethane, fluorine and bromine groups are introduced into the structure of the waterborne polyurethane, and the resultant waterborne polyurethane exhibits good moisture-proof and flame-retardant performance due to the containing of fluorine and bromine atoms.

The present disclosure provides a waterborne polyurethane, which is prepared from raw materials comprising, in parts by mass, 15-40 parts of a polyisocyanate monomer, 45-65 parts of a polymer polyol, 5-25 parts of a fluorine-containing modified monomer, a solid Lewis acid catalyst, 0.5-8 parts of a small-molecule chain extender, 3-10 parts of an ionic hydrophilic chain extender, more than 0 and not more than 12 parts of an ionic neutralizer, and water, wherein a mass ratio of the fluorine-containing modified monomer to the solid Lewis acid catalyst is in the range of 1:0.005-0.05, and the fluorine-containing modified monomer is the (2,2-dimethyl-1,3-dioxolan-4-yl)methyl 2-bromo-2,2-difluoroacetate as described in the aforementioned solutions.

The raw materials for preparing the waterborne polyurethane according to the present disclosure include, in parts by mass, 15-40 parts, preferably 20-35 parts, and more preferably 25-30 parts of the polyisocyanate monomer. In some embodiments of the present disclosure, the polyisocyanate monomer is an aliphatic, alicyclic, aromatic or araliphatic polyisocyanate. In some embodiments, the polyisocyanate monomer has a functionality of ≥2. In the present disclosure, there is no special requirement on the specific types of the aliphatic, alicyclic, aromatic or araliphatic polyisocyanates, and aliphatic, alicyclic, aromatic or araliphatic polyisocyanates well known in the art may be used. In some embodiments of the present disclosure, the polyisocyanate may specifically be hexamethylene diisocyanate, isophorone diisocyanate, toluene diisocyanate, diphenylmethane diisocyanate or dicyclohexylmethane diisocyanate.

Based on the parts by mass of the polyisocyanate monomer, the raw materials of the waterborne polyurethane according to the present disclosure include 45-65 parts, preferably 48-62 parts, and more preferably 51-58 parts of a polymer polyol. In some embodiments of the present disclosure, the polymer polyol has a molar mass of 500-4,000 g/mol, and more preferably 1,000-3,000 g/mol. In some embodiments, the polymer polyol has a functionality of ≥2. In the present disclosure, there is no special requirement on the specific type of the polymer polyol, and the polymer polyol may specifically be poly(hexanediol adipate) diol, poly(butylene adipate) diol, poly(ethylene glycol adipate) diol, poly(neopentyl glycol adipate) diol, poly[di(ethylene glycol) adipate)] diol, poly(caprolactone) diol, poly(hexanediol carbonate) diol, polyethylene glycol, polypropylene glycol or polytetrahydrofuran ether glycol.

Based on the parts by mass of the polyisocyanate monomer, the raw materials for preparing the waterborne polyurethane according to the present disclosure includes 5-25 parts, preferably 8-22 parts, and more preferably 10-18 parts of a fluorine-containing modified monomer. In the present disclosure, the fluorine-containing modified monomer is the (2,2-dimethyl-1,3-dioxolan-4-yl)methyl 2-bromo-2,2-difluoroacetate as described in the aforementioned solutions.

The raw materials for preparing the waterborne polyurethane according to the present disclosure includes a solid Lewis acid catalyst, and in some embodiments a mass ratio of the fluorine-containing modified monomer to the solid Lewis acid catalyst is in the range of 1:0.005-0.05, preferably 1:0.01-0.04, and more preferably 1:0.02-0.03. In some embodiments of the present disclosure, the solid Lewis acid catalyst is zirconium tetrachloride, aluminum trichloride or zinc dichloride.

Based on the parts by mass of the polyisocyanate monomer, the raw materials for preparing the waterborne polyurethane according to the present disclosure includes 0.5-8 parts, preferably 1-7 parts, and more preferably 3-5 parts of a small-molecule chain extender. In some embodiments of the present disclosure, the small-molecule chain extender is a small-molecule chain extender of polyhydroxy compound with a molar mass of less than 400 g/mol and a functionality of 2 to 4. In the present disclosure, the small-molecule chain extender may specifically be ethylene glycol, 1,4-butanediol, neopentyl glycol, diethylene glycol, 3-methylpentanediol, propanediol, 2-methylpropanediol, 1,6-hexanediol or trimethylolpropane.

Based on the parts by mass of the polyisocyanate monomer, the raw materials for preparing the waterborne polyurethane according to the present disclosure includes 3-10 parts, preferably 4-8 parts, and more preferably 5-6 parts of an ionic hydrophilic chain extender. In some embodiments of the present disclosure, the ionic hydrophilic chain extender is an ionic or latent ionic hydrophilic chain extender with a hydroxyl or amino group, which has a functionality of 2 to 4 in some embodiments. In the present disclosure, there is no special requirement on the specific type of the ionic hydrophilic chain extender, and any ionic hydrophilic chain extender well known in the art that meets the aforementioned conditions may be used. The specific ionic hydrophilic chain extender may be N-methyldiethanolamine, dimethylolpropionic acid, dimethylolbutyric acid, sodium ethylenediamine ethanesulfonate, sodium 1,4-dihydroxybutane-2-sulfonate, or a $\alpha,\omega$-polypropylene glycol-diamine-sulfopropyl sodium salt.

Based on the parts by mass of the polyisocyanate monomer, the raw materials for preparing the waterborne polyurethane according to the present disclosure includes more than 0 and not more than 12 parts, preferably 2-10 parts, and more preferably 4-8 parts of an ionic neutralizer. In the present disclosure, there is no special requirement on the specific type of the electric neutralizer, and an electric neutralizer well known in the art may be used. The specific electric neutralizer may be dimethyl ether sulfate, glacial acetic acid, triethylamine, triethanolamine, dimethyl ethanolamine, diisopropylethylamine, or sodium hydroxide.

The raw materials for preparing the waterborne polyurethane according to the present disclosure, include water. In the present disclosure, there is no special requirement on the dosage of water. In some embodiments, the dosage is determined according to the solid content of the waterborne polyurethane. In some embodiments of the present disclosure, a solid content of the waterborne polyurethane is in the range of 30-40%.

In some embodiments of the present disclosure, a method for preparing the waterborne polyurethane includes the following steps:

(1) mixing a part of the polyisocyanate monomer, the fluorine-containing modified monomer and the solid Lewis acid catalyst, and subjecting the resulting mixture to a first nucleophilic addition reaction to obtain a NCO-terminated fluorinated prepolymer;

(2) mixing the polymer polyol with the rest of the polyisocyanate monomer, subjecting the resulting mixture to a second nucleophilic addition reaction to obtain a second nucleophilic addition reaction product, adding the NCO-terminated fluorinated prepolymer, the small-molecule chain extender and the ionic hydrophilic chain extender into the second nucleophilic addition reaction product and subjecting the resulting mixture to a chain extension reaction to obtain a chain extension reaction product, adding a first catalyst into the chain extension reaction product, and subjecting the resulting mixture to a third nucleophilic addition reaction to obtain a fluorinated and modified polyurethane prepolymer; and (3) adding the ionic neutralizer into the fluorinated and modified polyurethane prepolymer, and subjecting the resulting mixture to a neutralization reaction, and then adding water thereto for emulsification and dispersion to obtain the waterborne polyurethane.

In the present disclosure, a part of the polyisocyanate is mixed with the fluorine-containing modified monomer and the solid Lewis acid catalyst, and the resulting mixture is subjected to a first nucleophilic addition reaction to obtain a NCO-terminated fluorinated prepolymer.

In some embodiments of the present disclosure, the part of the polyisocyanate monomer is 20%-65%, more preferably 30%-55%, and further more preferably 40%-50% of the total mass of polyisocyanate monomer. In some embodiments of the present disclosure, the first nucleophilic addition reaction is performed at a temperature of 50-70° C., and more preferably 55-65° C. In some embodiments, the first nucleophilic addition reaction is performed for 1-2 h. In some embodiments, the first nucleophilic addition reaction is carried out under the protection of nitrogen. In the present disclosure, during the first nucleophilic addition reaction, the fluorine-containing modified monomer is deprotected under the action of the solid Lewis acid catalyst, and the —NCO group of the polyisocyanate and the —OH group obtained after the deprotection of the fluorine-containing modified monomer (i.e., (2,2-dimethyl-1,3-dioxolan-4-yl)methyl 2-bromo-2,2-difluoroacetate) undergo a nucleophilic addition reaction to obtain a NCO-terminated fluorinated prepolymer.

In the present disclosure, after the NCO-terminated fluorinated prepolymer is obtained, the polymer polyol is mixed with the rest of the polyisocyanate monomer, and the resulting mixture is subjected to a second nucleophilic addition reaction; the NCO-terminated fluorinated prepolymer, the small-molecule chain extender and the ionic hydrophilic chain extender are added to the second nucleophilic addition reaction product, and the resulting mixture is subjected to a chain extension reaction; the first catalyst is added to the chain extension reaction product, and the resulting mixture is subjected to a third nucleophilic addition reaction to obtain a fluorinated and modified polyurethane prepolymer.

In some embodiments of the present disclosure, before the second nucleophilic addition reaction, the polymer polyol is dehydrated in vacuum. In some embodiments, the vacuum dehydration is performed at a temperature of 105-120° C., and preferably 110-115° C. In some embodiments, the vacuum dehydration is performed for 1-2 h. In some embodiments of the present disclosure, the polymer polyol is mixed with the rest of polyisocyanate at a temperature of 55-75° C. In some embodiments of the present disclosure, the second nucleophilic addition reaction is performed at a temperature of 60-90° C., and preferably 70-80° C. In some embodiments, the second nucleophilic addition reaction is performed at a constant temperature for 1-2 h. In the present disclosure, during the second nucleophilic addition reaction, the —NCO group of polyisocyanate and the —OH group of polymer polyol undergo a nucleophilic addition reaction to obtain a NCO-terminated polyurethane prepolymer.

In the present disclosure, after the second nucleophilic addition reaction is completed, the NCO-terminated fluorinated prepolymer, the small-molecule chain extender and the ionic hydrophilic chain extender are added to the second nucleophilic addition reaction product, and the resulting mixture is subjected to a chain extension reaction; the catalyst is added to the chain extension reaction product, and the resulting mixture is subjected to a third nucleophilic addition reaction to obtain a fluorinated and modified polyurethane prepolymer.

In some embodiments of the present disclosure, the chain extension reaction is performed at a temperature of 60-90° C., and preferably 70-80° C. In some embodiments, the chain extension reaction is performed for 1-1.5 h.

In the present disclosure, there is no special requirement on the type of the first catalyst, and a catalyst well known in the art for preparing the waterborne polyurethane may be used. In an embodiment of the present disclosure, the first catalyst is an organic bismuth catalyst. In some embodiments of the present disclosure, the dosage of the first catalyst is 0.05-0.1%, and preferably 0.07-0.08% of the mass of the chain extension reaction product.

In some embodiments of the present disclosure, the third nucleophilic addition reaction is performed at a temperature of 60-75° C., and preferably 70-75° C. In some embodiments, the third nucleophilic addition reaction is performed for 2-3 h. In the present disclosure, during the third nucleophilic addition reaction, the nucleophilic addition reaction of the —NCO group and the —OH group is continuously carried out to form a NCO-terminated, fluorinated and modified polyurethane prepolymer.

In some embodiments of the present disclosure, before the chain extension reaction and the third nucleophilic addition reaction, acetone solvent is added according to specific experimental conditions to reduce the viscosity of the reaction system, and the dosage of the solvent is 5-30% of the mass of the current reactants, which is common knowledge in the art.

In the present disclosure, after the third nucleophilic addition reaction is completed, the ionic neutralizer is added to the fluorinated and modified polyurethane prepolymer and the resulting mixture is subjected to a neutralization reaction. After the neutralization reaction is completed, water is added thereto for emulsification and dispersion, so as to obtain the waterborne polyurethane.

In some embodiments of the present disclosure, the neutralization reaction is performed at a temperature of 30-40° C., and preferably 33-38° C. In some embodiments, the neutralization reaction is performed for 5-20 min. In some embodiments of the present disclosure, water is deionized water. In some embodiments, the dosage of water is in such a manner that the solid content of the final waterborne polyurethane emulsion (after removing the acetone solvent) is ensured to be 30-40%. In some embodiments of the present disclosure, the emulsification and dispersion is carried out under a high-speed stirring. In some embodiments, the high-speed stirring has a rotation speed of 800-2,000 rpm.

After the emulsification and dispersion are completed, the resultant emulsion is the waterborne polyurethane, or those skilled in the art could obtain an emulsion of the waterborne polyurethane by adding a diamine chain extender into the resultant emulsion as required and subjecting the resulting mixture to a post-chain extension reaction.

In the present disclosure, there is no special requirement on the specific type of the diamine chain extender, and a diamine chain extender well known in the art may be used. In some embodiments of the present disclosure, the molar dosage of the diamine chain extender is not more than 60% of the residual molar amount of NCO. In some embodiments of the present disclosure, the post-extension chain reaction is performed for 5-10 min.

The (2,2-dimethyl-1,3-dioxolan-4-yl)methyl 2-bromo-2,2-difluoroacetate, waterborne polyurethane and preparation methods thereof according to the present disclosure will be described in detail in connection with the following examples, but they should not be understood as limiting the claimed scope of the present disclosure.

EXAMPLE 1

Into a 1 L reaction vessel equipped with a thermometer, a reflux condensing tube, a water separator and a stirer, 203 g of ethyl 2-bromo-2,2-difluoroacetate, 260 g of Solketal and 3.2 g of sodium methoxide were added, and the resulting mixture was reacted at 115° C. for 12 hours. The obtained reaction product was then distilled under reduced pressure, and a fraction under conditions of 104-106° C./25 mmHg was collected, obtaining 285.5 g of (2,2-dimethyl-1,3-dioxolan-4-yl)methyl 2-bromo-2,2-difluoroacetate having the structure of Formula I, with a yield of 98.8% and a purity of 99.5%,

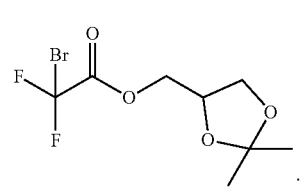

Formula I

Figure 2:
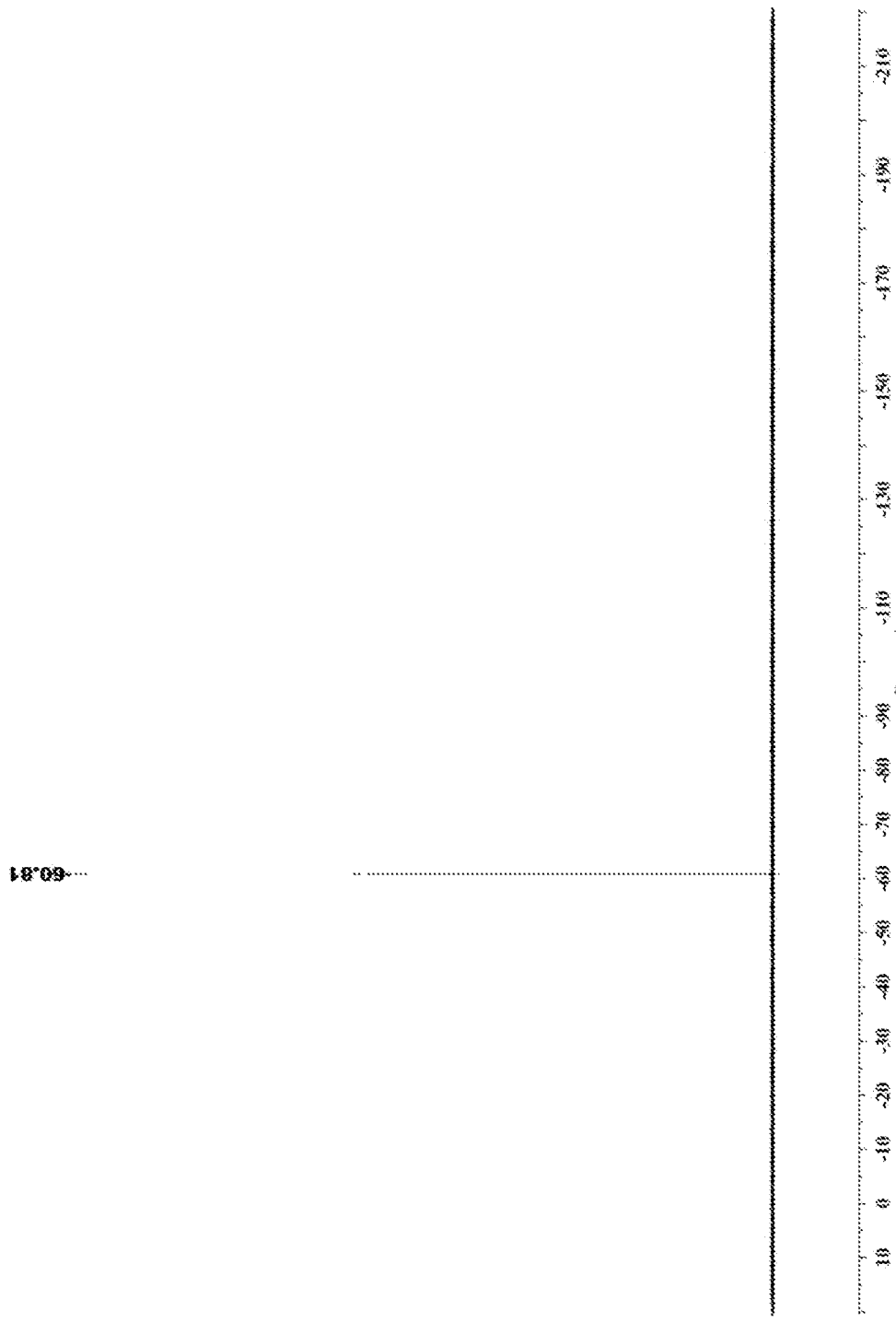
FIG. 2 shows the fluorine-nuclear magnetic resonance spectrum ($^{19}$F NMR) of the (2,2-dimethyl-1,3-dioxolan-4-yl)methyl 2-bromo-2,2-difluoroacetate as prepared in Example 1.

The (2,2-dimethyl-1,3-dioxolan-4-yl)methyl 2-bromo-2,2-difluoroacetate prepared in Example 1 was subjected to a nuclear magnetic resonance analysis. The results are shown in FIGS. 1-2, in which FIG. 1 shows the hydrogen-nuclear magnetic resonance spectrum and FIG. 2 shows the fluorine-nuclear magnetic resonance spectrum. It can be seen from FIGS. 1-2 that the (2,2-dimethyl-1,3-dioxolan-4-yl)methyl 2-bromo-2,2-difluoroacetate prepared in Example 1 of the present disclosure was confirmed to have the expected structure.

NMR characterization data:
$^1$H NMR (500 MHz, CDCl$_3$) δ 4.43-4.30(m, 3H), 4.12 (ddd, J=10.3, 4.4, 1.7 Hz, 1H), 3.87-3.81 (m, 1H), 1.44 (s, 3H), 1.38 (s, 3H).
$^{19}$F NMR (471 MHz, CDCl$_3$) δ-60.81.

EXAMPLE 2

Into a 1 L reaction vessel equipped with a thermometer, a reflux condensing tube, a water separator and a stirrer, 189 g of methyl 2-bromo-2,2-difluoroacetate, 260 g of Solketal and 1.89 g of potassium hydroxide were added, and the resulting mixture was reacted at 125° C. for 8 hours. The obtained reaction product was then distilled under reduced pressure, and a fraction under conditions of 104-106° C./25 mmHg was collected, obtaining 283.3 g of (2,2-dimethyl-1,3-dioxolan-4-yl)methyl 2-bromo-2,2-difluoroacetate, with a yield of 98.0% and a purity of 99.5%.

EXAMPLE 3

Into a 1 L reaction vessel equipped with a thermometer, a reflux condensing tube, a water separator and a stirrer, 189 g of methyl 2-bromo-2,2-difluoroacetate, 660 g of Solketal, 3.2 g of potassium bicarbonate and 3.2 g of potassium carbonate were added, and the resulting mixture was reacted at 80° C. for 25 hours. The obtained reaction product was distilled under reduced pressure, a fraction under conditions of 104-106° C./25 mmHg was collected, obtaining 282.1 g of (2,2-dimethyl-1,3-dioxolan-4-yl)methyl 2-bromo-2,2-difluoroacetate, with a yield of 97.6% and a purity of 99.4%.

EXAMPLE 4

Into a 1 L reaction vessel equipped with a thermometer, a reflux condensing tube, a water separator and a stirrer, 203 g of ethyl 2-bromo-2,2-difluoroacetate, 350 g of Solketal, 3.2 g of sodium hydroxide, 3.2 g of sodium carbonate and 3.2 g of sodium bicarbonate were added, and the resulting mixture was reacted at 140° C. for 5 hours. The obtained reaction product was then distilled under reduced pressure, a fraction under conditions of 104-106° C./25 mmHg was collected, obtaining 280.1 g of (2,2-dimethyl-1,3-dioxolan-4-yl)methyl 2-bromo-2,2-difluoroacetate, with a yield of 96.9% and a purity of 99.3%.

EXAMPLE 5

Into a 1 L reaction vessel equipped with a thermometer, a reflux condensing tube, a water separator and a stirrer, 189 g of methyl 2-bromo-2,2-difluoroacetate, 350 g of Solketal and 5.2 g of sodium hydride, and the resulting mixture was reacted at 110° C. for 10 hours. The obtained reaction product was distilled under reduced pressure to collect a fraction under conditions of 104-106° C./25 mmHg, obtaining 284.1 g of (2,2-dimethyl-1,3-dioxolan-4-yl)methyl 2-bromo-2,2-difluoroacetate, with a yield of 98.3% and a purity of 99.6%.

The (2,2-dimethyl-1,3-dioxolan-4-yl)methyl 2-bromo-2,2-difluoroacetate prepared in each of Examples 2-5 was subjected to a nuclear magnetic resonance analysis. The results show that the (2,2-dimethyl-1,3-dioxolan-4-yl)methyl 2-bromo-2,2-difluoroacetate prepared in Examples 2-5 of the present disclosure were confirmed to have the expected structure.

Use Example 1 a) 15 g of toluene diisocyanate, 0.05 g of zirconium tetrachloride and 10 g of (2,2-dimethyl-1,3-dioxolan-4-yl)methyl 2-bromo-2,2-difluoroacetate were added, and nitrogen was introduced for protection. The resulting mixture was reacted under stirring at 50° C. for 1 h, obtaining an NCO group (from an isocyanate)-terminated fluorinated prepolymer.

b) 58 g of polypropylene glycol (Mn=2,000) was heated and dehydrated in vacuum at 105° C. for 1 h, and cooled to 55° C. 11 g of toluene diisocyanate was then added thereto, and the resulting mixture was reacted at a constant temperature of 80° C. for 1 h. The aforementioned NCO-terminated fluorinated prepolymer obtained in a) was added thereto. 3 g of neopentyl glycol, 5 g of dimethylolpropionic acid and 10 g of acetone were added thereto, and the resulting mixture was subjected to a chain extension reaction at 80° C. for 1 h. 0.08 g of an organic bismuth catalyst and 8 g of acetone were added thereto, and the resulting mixture was reacted at 75° C. for 2 h. The resulting reaction system was cooled to 30° C. 3.5 g of triethylamine was added thereto, and the resulting mixture was reacted for 5 min. 234 g of deionized water was added under a stirring with a high speed of 2,000 rpm for emulsification and dispersion, and acetone therein was removed under reduced pressure to obtain the waterborne polyurethane with a solid content of 30%.

Comparative Use Example 1

Different from Use Example 1, (2,2-dimethyl-1,3-dioxolan-4-yl)methyl 2-bromo-2,2-difluoroacetate was not used in this example, and the specific procedures were as follows:

58 g of polypropylene glycol (Mn=2,000) was heated and dehydrated in vacuum at 105° C. for 1 h, cooled to 55° C. 26 g of toluene diisocyanate was then added thereto, and the resulting mixture was reacted at a constant temperature of 80° C. for 1 h. 5.8 g of neopentyl glycol, 5 g of dimethylolpropionic acid and 10 g of acetone were added thereto, and the resulting mixture was reacted at 80° C. for 1 h. 0.08 g of an organic bismuth catalyst and 8 g of acetone were added thereto, and the resulting mixture was reacted at 75° C. for 2 h. The resulting reaction system was cooled to 30° C. 3.5 g of triethylamine was added thereto, and the resulting mixture was reacted for 5 min. 234 g of deionized water was added under a stirring with a high speed of 2,000 rpm for emulsification and dispersion, and acetone therein was removed under reduced pressure to obtain the waterborne polyurethane with a solid content of 30%.

PERFORMANCE TEST (1) Water Absorption Rate Test a) Preparation of polyurethane Adhesive Film Firstly, the waterborne polyurethane was poured into a polytetrafluoroethylene film former, ensuring that there were no bubbles, and then dried at room temperature for 48 h, then at 60° C. for 48 h, and finally at 80° C. for 24 h, obtaining the waterborne polyurethane adhesive film.

b) Water Absorption Rate Test

The waterborne polyurethane adhesive film was cut into samples of 2 cm×2 cm, weighed and recorded as initial mass $m_0$. The sample was then completely immersed in deionized water for 24 h, then taken out, wiped with filter paper to remove the water from the surface of the immersed sample, subsequently weighed, and recorded as mass $m_1$ after water absorption; the water absorption rate W of polyurethane adhesive film sample was calculated according to Equation (2), and three samples were tested to take an average value, $$W = \frac{m_1 - m_0}{m_0} \times 100\%. \qquad \text{Equation (2)}$$

2) Flame-Retardant Performance Test

An oxygen index of the polyurethane adhesive film was determined according to the National Standard "GB/T 5455-2014 Textiles-Burning behavior-Determination of damaged Length, afterglow time and afterflame time of vertically oriented specimens".

The water resistance and flame-retardant performance of the waterborne polyurethane prepared in Use Example 1 and Comparative Use Example 1 were tested. The test results are shown in Table 1.

TABLE 1

Performance of waterborne polyurethane as prepared in Use Example 1 and Comparative Use Example 1

| | Water absorption rate/% | Oxygen index |
|---|---|---|
| Use Example 1 | 10% | 25% |
| Comparative Use Example 1 | 25% | 17% |

In Table 1, the lower water absorption rate indicates better water resistance and better waterproof performance, and the higher oxygen index indicates better flame-retardant performance. It can be seen from the results in Table 1 that the water resistance and flame-retardant performance of the fluorinated and modified polyurethane is obviously better than that of the samples that are not subjected to fluorinating modification. It indicates that in the present disclosure, the substituents at C2 position are designed as two fluorine atoms and one bromine atom, so that the modified auxiliary monomer exhibits further improved moisture-proof and flame-retardant performance and meanwhile certain hydrophobicity. When such monomer is used for preparing the waterborne polyurethane, the resultant waterborne polyurethane exhibits good moisture-proof and flame-retardant performance.

The above description is only preferred embodiments of the present disclosure. It should be pointed out that, for those of ordinary skill in the art, several improvements and modifications could be made without departing from the principle of the present disclosure. These improvements and modifications should also be considered as falling within the claimed scope of the present disclosure.

What is claimed is:

1. A waterborne polyurethane, which is prepared from raw materials comprising, in parts by mass:

15-40 parts of a polyisocyanate monomer, 45-65 parts of a polymer polyol, 5-25 parts of a fluorine-containing modified monomer, a solid Lewis acid catalyst, 0.5-8 parts of a small-molecule chain extender, 3-10 parts of an ionic hydrophilic chain extender, more than 0 and not more than 12 parts of an ionic neutralizer, and water, wherein a mass ratio of the fluorine-containing modified monomer to the solid Lewis acid catalyst is in a range of 1:0.005-0.05; and the fluorine-containing modified monomer has a structure of Formula I:

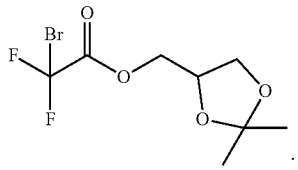

Formula I

2. A method for preparing the waterborne polyurethane as claimed in claim 1, comprising (1) mixing a part of the polyisocyanate monomer, the fluorine-containing modified monomer and the solid Lewis acid catalyst, and subjecting the resulting mixture to a first nucleophilic addition reaction to obtain a NCO-terminated fluorinated prepolymer;

(2) mixing the polymer polyol with the rest of the polyisocyanate monomer, subjecting the resulting mixture to a second nucleophilic addition reaction to obtain a second nucleophilic addition reaction product; adding the NCO-terminated fluorinated prepolymer, the small-molecule chain extender and the ionic hydrophilic chain extender into the second nucleophilic addition reaction product, and subjecting the resulting mixture to a chain extension reaction, to obtain a chain extension reaction product, adding a first catalyst into the chain extension reaction product, and subjecting the resulting mixture to a third nucleophilic addition reaction to obtain a fluorinated and modified polyurethane prepolymer; and (3) adding the ionic neutralizer into the fluorinated and modified polyurethane prepolymer, and subjecting the resulting mixture to a neutralization reaction, and then adding water thereto for emulsification and dispersion to obtain the waterborne polyurethane.

* * * * *